United States Patent
Briggs, III (10) Patent No.: US 6,994,088 B2
(45) Date of Patent: Feb. 7, 2006

(54) DEVICE AND METHOD FOR SECURING TRACHEOSTOMY TUBE ATTACHMENTS

(76) Inventor: Stephen W. Briggs, III, P.O. Box 1958, Loomis, CA (US) 95650

( * ) Notice: Subject to any disclaimer, the term of this patent is extended or adjusted under 35 U.S.C. 154(b) by 0 days.

(21) Appl. No.: 10/762,772

(22) Filed: Jan. 22, 2004

(65) Prior Publication Data

US 2005/0161047 A1    Jul. 28, 2005

(51) Int. Cl.
*A61M 16/00*    (2006.01)

(52) U.S. Cl. .............................. 128/207.17; 128/207.14
(58) Field of Classification Search .......... 128/207.14, 128/207.17, DIG. 26, 206.26, 207.16, 911, 128/912, DIG. 23, 200.26, 207.29, 201.11, 128/207.15, 202.27; 604/174, 179; 2/137, 2/170, 59, 181.2; 623/9; 24/163 R
See application file for complete search history.

(56) References Cited

U.S. PATENT DOCUMENTS

| | | | |
|---|---|---|---|
| 3,039,469 A | 6/1962 | Fountain | |
| 3,927,676 A | 12/1975 | Schultz | |
| 4,470,176 A * | 9/1984 | Vermeulen et al. | ....... 24/163 R |
| 5,282,463 A | 2/1994 | Hammersley | |
| 5,305,742 A | 4/1994 | Styers et al. | |
| 5,357,952 A | 10/1994 | Schuster et al. | |
| 5,368,023 A | 11/1994 | Wolf | |
| 5,471,980 A * | 12/1995 | Varner | ................... 128/207.17 |
| 5,501,216 A | 3/1996 | Byrd | |
| 5,529,062 A | 6/1996 | Byrd | |
| 5,671,732 A | 9/1997 | Bowen | |
| 5,782,236 A * | 7/1998 | Ess | ........................ 128/207.17 |
| 5,839,437 A | 11/1998 | Briggs, III | |
| 6,047,699 A * | 4/2000 | Ryatt et al. | ............. 128/207.17 |
| 6,394,092 B1 * | 5/2002 | Barrett et al. | ........... 128/207.17 |
| 6,612,309 B1 * | 9/2003 | Ancona | ................. 128/201.17 |
| 6,722,369 B1 * | 4/2004 | Kron | ..................... 128/207.17 |

* cited by examiner

*Primary Examiner*—Teena Mitchell
(74) *Attorney, Agent, or Firm*—Knobbe, Martens, Olson & Bear, LLP (57) ABSTRACT

A retainer is provided comprising a ring configured to fit over a readily available tracheostomy tube and be securable thereto, and further having cooperating straps configured to extend around and secure an auxiliary device coupled to the tracheostomy tube, such as a ventilator tube. The retainer is configured to be selectively and easily attachable to existing tracheostomy tubes to provide a platform for securing an auxiliary device.

27 Claims, 6 Drawing Sheets

DEVICE AND METHOD FOR SECURING TRACHEOSTOMY TUBE ATTACHMENTS

BACKGROUND OF THE INVENTION

1. Field of the Invention

The current invention relates to medical devices, and more specifically, to a securement device for inhibiting unintentional disconnection of an auxiliary device attached to a tracheostomy tube.

2. Description of the Related Art

Tracheotomy is a surgical procedure in which an incision, called a tracheostomy, is made into the trachea through the neck tissues that forms a temporary or permanent opening, called a stoma. A tracheostomy tube is inserted through the opening to allow passage of air and removal of secretions. The tracheostomy tube allows air to flow through the tube and into the patient's lungs and further allows passage of other medical instruments into the trachea and connected organs.

Once the tracheostomy tube has been inserted it is important that the position of the tube be stabilized such that it is not inadvertently withdrawn from the trachea, and such that the tube is otherwise positioned to function properly. Currently, tracheostomy tubes typically have a laterally extending flange surface configured to extend parallel to the front portion of the patient's neck when the tube is installed. The flange generally has two slots for connecting with a strip or band to encircle the patient's neck to hold the tracheostomy tube securely in place.

Oftentimes, an auxiliary device is connected to the tracheostomy tube. Such auxiliary devices are desirable for monitoring a patient's breathing or for aspirating secretions. It is desirable that any auxiliary device remains securely attached to the tracheostomy tube to inhibit inadvertent separation. This is especially important with young children who may attempt to remove such auxiliary devices. Moreover, it is advantageous to secure the auxiliary devices during sleep periods, during which a patient may inadvertently disconnect the auxiliary device.

SUMMARY OF THE INVENTION

It is therefore an object of the present invention to provide a simple device that is easily attachable to current tracheostomy tubes and collars and which is configured to securely attach an auxiliary device to a tracheostomy tube. The present invention results, in part, from the realization that many current tracheostomy tubes are configured with a generally round tube and have a laterally extending flange surface configured with slots designed to receive the straps of a collar to secure the tracheostomy tube to a patient's neck. By taking advantage of the typical structure of modem tracheostomy tubes, embodiments of the present invention are configured to be used with a wide variety of tracheostomy tubes and provide the added advantage of securing an auxiliary device to a readily available tracheostomy tube.

According to one embodiment, an apparatus is provided for securing an auxiliary device to a tracheostomy tube. The apparatus comprises a ring having a pair of opposed extensions defining strap holds, and further having a pair of secondary strap holds. A void within the ring is configured to allow passage of a tracheostomy tube through the right. A pair of auxiliary device straps are affixed to each of the secondary strap holds, the auxiliary straps configured so that, when the tracheostomy tube extends through the rnig void, the auxiliary straps extend around an auxiliary device that is fit onto the tracheostomy tube so as to maintain a maximum spatial relationship between the auxiliary device and the ring. The auxiliary device straps can be configured with fastening elements to releasably secure the auxiliary device straps together, such as hook and loop fastener, for example. A tracheostomy collar can be provided having a neck strap and the ring can be secured to the tracheostomy collar by the neck strap. In one embodiment, the neck strap connects to the tracheostomy collar and the, strap holds of the ring. In some embodiments, the ring has a major axis extending between the strap holds and a minor axis extending between the secondary strap holds, and the major axis is greater than the minor axis.

According to another embodiment, a method of securing an auxiliary device to a flanged tracheostomy tube comprises the steps of providing a flanged tracheostomy tube; providing an auxiliary device; providing a tracheostomy collar having a neck strap; providing a retainer configured to fit over the tracheostomy tube, the retainer having a retainer strap configured for releasable engagement with the auxiliary device, and further having two or more strap holds configured to receive the neck strap; fitting the retainer over the tracheostomy tube; securing thee neck strap to the flanged tracheostomy tube and to the retainer thereby securing the retainer to the tracheostomy tube; engaging the auxiliary device with the tracheostomy tube; and securing the retainer to the auxiliary device with the retainer strap. Optionally, the neck strap can pass through slots on the tracheostomy tube and also pass through the strap holds on the retainer. In addition, the method can further comprise the step of fastening a pair of retainer straps having a hook and loop fastening closure around the auxiliary device. Finally, the neck strap can connect to both the tracheostomy tube and the strap holds.

DETAILED DESCRIPTION OF THE PREFERRED EMBODIMENTS

In the following description, reference is made to the accompanying drawings which form a part of this written description which show, by way of illustration, specific embodiments in which the invention can be practiced. It is to be understood that other embodiments may be utilized and structural changes may be made without departing from the scope of the present invention. Where possible, the same reference numbers will be used throughout the drawings to refer to the same or like components. Numerous specific details are set forth in order to provide a thorough understanding of specific embodiments; however, it is to be understood that the present invention may be practiced without the specific details or with certain alternative equivalent devices and methods to those described herein. In other instances, well-known methods, procedures, components and devices have not been described in detail so as not to unnecessarily obscure aspects of the present invention.

Figure 1:
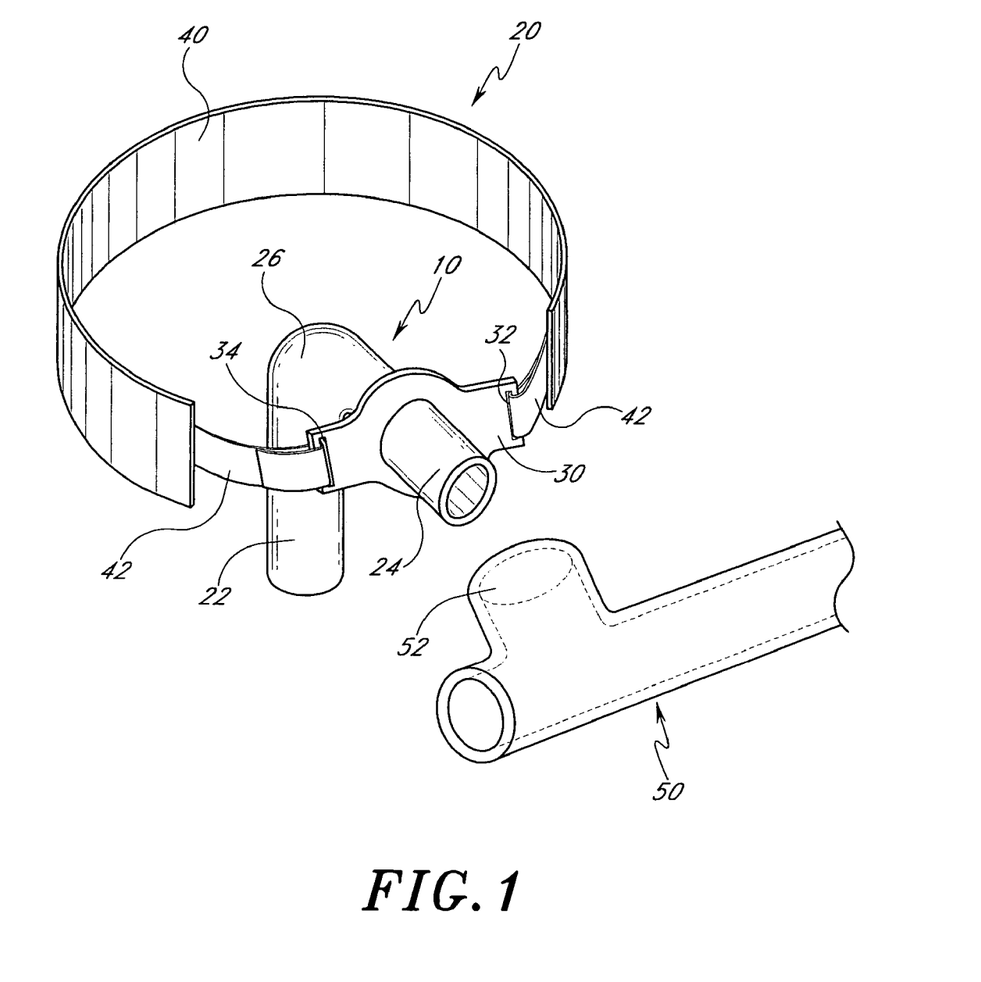
FIG. 1 illustrates a perspective view of one embodiment of a tracheostomy tube and a collar.

FIG. 1 illustrates a typical, commercially available tracheostomy tube 10 and a collar 20 designed to hold the tracheostomy tube 10 in place. The tracheostomy tube ("trach tube") generally comprises a down tube 22 and an out tube 24 connected by an elbow 26. Typically, the down tube 22, out tube 24, and elbow 26 are of unitary construction, however, it is conceivable that these components could be separate and connected to form a trach tube. A flange 30, which is also typically formed integral with the trach tube, extends from the out tube 24 and defines a generally planar surface extending perpendicular to the out tube 24. The typical flange 30 defines two apertures 32, 34. As used herein, the terms tracheostomy tube, trach tube, and endotracheal tube are used interchangeably and all refer to a device configured to reside at least partially within a patient's trachea and to provide a conduit for breathing, and are used in their broadest sense.

With continued reference to FIG. 1, the collar 20 typically comprises a neck band 40 and one or more straps 42 configured to attach the collar 20 to the flange 30 at the flange apertures 32. In many available collars 20, the straps 42 are flexible and oftentimes formed of a resilient material. They may be secured to the flange 30 in any of a number of methods; however, one common method secures a collar 20 to a trach tube flange 30 by passing the straps 42 through the flange apertures 32, and then fastening the strap 42 either to itself, or to another portion of the collar 20. The strap 42 is often fastened by configuring the neck strap 42 with hook and loop fastener. Of course, other methods of securing the collar 20 to the flange 30 are possible, such as by using tie strings, snaps, or other suitable releasable fastening connectors.

When worn by a patient, the flange 30 usually rests against the patient's neck and thereby stabilizes the trach tube 10 from unintentional movement, which can cause discomfort to the patient. Moreover, during installation, the trach tube 10 is inserted until the flange 30 rests against the patient's neck which provides for repeatable placement. The neck strap is preferably configured to maintain the trach tube 10 in its desired position.

Oftentimes, it is desirable or necessary to attach an auxiliary device 50 to a trach tube 10. The auxiliary device 50 may be any of a number of useful devices, such as, for example, a ventilation tube, a heat or moisture exchanger, a filter, or the like. The auxiliary device 50 typically comprises an attachment portion 52 configured to engage the out tube 24. The auxiliary device 50 attachment portion 52 may be configured as a cylinder with a diameter slightly larger than the out tube 24 such that the attachment portion 52 may slide engagingly over the out tube 24. In many cases, the auxiliary device 50 is attached by friction. However, it is desirable in certain circumstances to secure the auxiliary device 50 to the trach tube 10 by a more secure device and method.

Figure 2:
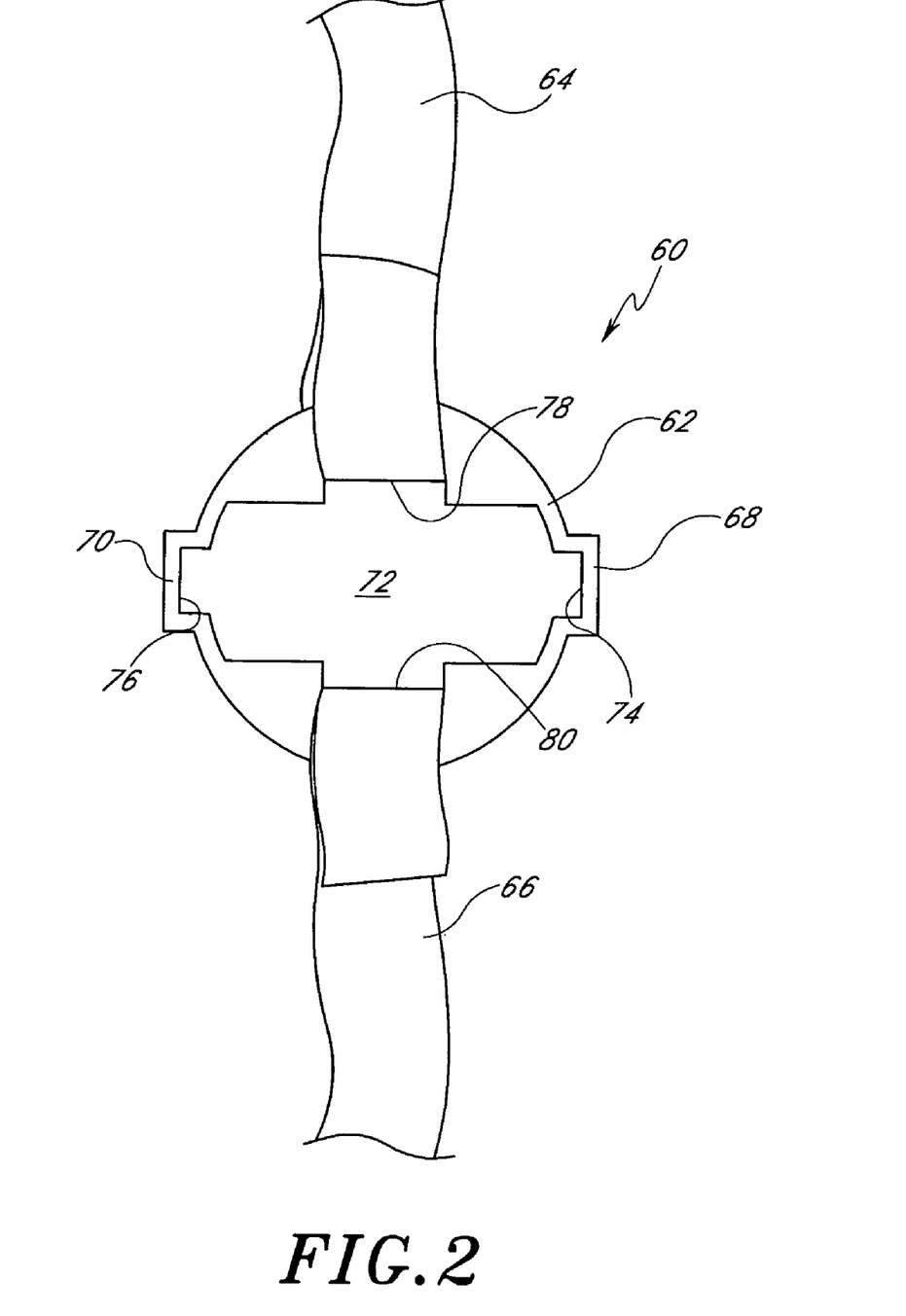
FIG. 2 is a plan view of one embodiment of a securement device for use with a tracheostomy tube.

Referring to FIG. 2, one embodiment of a tracheostomy tube attachment securing device, or retainer 60, is shown. In the illustrated embodiment, the retainer 60 comprises a generally circular ring 62, an upper strap 64, and a lower strap 66. As used herein, the term "ring" is a broad term and is used to describe any regular or irregular peripheral shape that defines an opening through its center. For example, a ring may be shaped as a circle, oval, rectangle, oblong, or any other regular or irregular shape. Moreover, a ring need not define a closed shape, but also includes open configurations, such as U-shaped or C-shaped configuration. In addition, the term "ring" also includes shapes that are selectively configurable, such as having a hinge, or one that is separable into two or more pieces. Likewise, the term strap is a broad term and is used herein to refer to any device that extends from the ring and is configured to secure, engage, be attached to, or otherwise hold onto another component.

The ring 62 illustrated in FIG. 2 defines a closed shape and generally defines a circle having two lateral extensions 68, 70. The interior of the ring 62 is configured with a void 72 dimensioned to allow a tracheostomy tube 10 to pass therethrough. The void 72 is further configured to cooperate with the lateral extensions 68, 70 to provide strap holds 74, 76. In addition, the void 72 cooperates with the ring 62 to define secondary strap holds 78, 80 configured to accommodate the upper strap 64 and the lower strap 66. In the illustrated embodiment, the upper strap 64 and the lower strap 66 are permanently attached to the ring 60. In one embodiment, the upper strap 64 passes through the void 72 and is then affixed to itself, such as by sewing, adhesives, or other mechanical or chemical bonding. The lower strap 66 is similarly attached to the ring 62. In other embodiments, the upper strap 64 and lower strap 66 are selectively removable from the ring 62, and may be attached through a releasable connection, such as hook and loop fastener.

The strap holds 74, 76 are preferably configured to allow a neck strap 42 provided with a standard tracheostomy collar 20, such as the one illustrated in FIG. 1, to engage the strap holds 74, 76 without causing the neck strap 42 to crease or fold. In one embodiment, this is accomplished by forming the strap holds 74, 76 to be at least the width of a standard neck strap 42 found on traditional tracheostomy collars 20, which allows the neck strap 42 to lay substantially flat through the strap holds 74, 76 without folding or creasing.

The ring 62 may be formed of any suitable material, such as polymers, metals, composites, or combinations thereof, and by any suitable method, such as injection molding or machining. In one preferred embodiment, the ring 62 is injection molded of a suitable polymer, such as polyethylene or polyurethane, for example. The upper strap 64 and lower strap 66 can be formed of any suitable material, such as nylon, plastic, or any other suitable textile or polymeric material. Of course, other materials for the various components will be readily apparent to those of skill in the art and the scope of the invention should not be limited to those specific materials or manufacturing processes disclosed herein.

Figure 3:
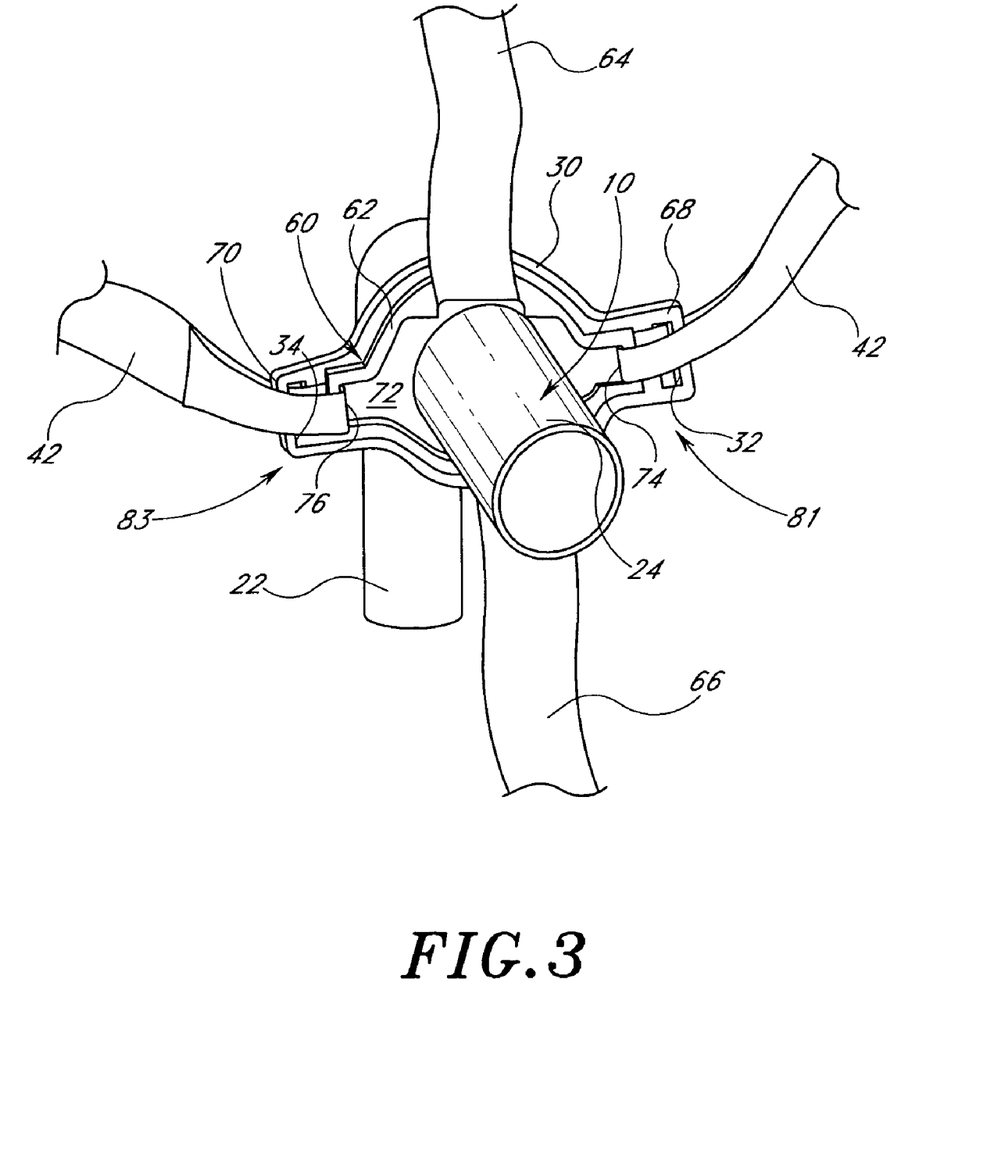
FIG. 3 is a perspective view of the securement device of FIG. 2 engaging a tracheostomy tube.

Referring to FIG. 3, the retainer 60 is illustrated secured to the trach tube 10. With the trach tube 10 inserted into the patient, the retainer 60 is slipped over the out tube 24. Referring to a first side 81 of the assembly, the neck strap 42 first passes through the flange aperture 32 by being inserted from the back of the flange 30 and exiting the front of the flange 30. The neck strap 42 then passes through the retainer void 72 from the rear of the retainer 60 and is then secured in any suitable manner. As discussed above, many tracheostomy collar neck straps 42 are secured by hook and loop fastener, snaps, or otherwise. However, for convenience, the remainder of this disclosure will use hook and loop fastener as an example. Once the neck strap 42 passes through the retainer 60, it engages the strap hold 74, which presents a substantially flat surface to inhibit the neck strap 42 from bending or folding along its longitudinal length. The neck strap 42 may be optionally routed back through the flange aperture 32, or it may simply pass over the flange 30 before it is secured. After the neck strap 42 has been routed through the flange aperture 32 and the retainer 60, it is tensioned appropriately and is secured to itself by hook and loop fastener.

The second side 83 of the assembly is configured in substantially the same way, with the neck strap 42 passing first through the flange aperture 34 from the back of the flange 30 and exiting the front of the flange 30. The neck strap 42 then passes through the void 72 from the back of the retainer 60 and exits the front of the retainer 60. The neck strap 42 can then either pass over the retainer 60 and flange 30 and be secured as illustrated in FIG. 3, or it may pass over the retainer 60 and back through the flange aperture 34 before it is secured. Thus, with the neck strap appropriately tensioned and secured, the neck strap 42 exerts a force on the retainer 60 that urges the retainer against the flange 30, thereby keeping the flange 30 against the patient.

As can be seen, the neck strap 42 passes through the flange apertures 32, 34 and can hold the flange 30 even in the absence of the retainer 60 as illustrated in FIG. 1. Hence, the neck strap 42 holds the flange 30 firmly in place whether or not the retainer 60 is present. Thus, a significant advantage of described embodiments is that the retainer 60 can be added and removed from a commercially available assembly quickly and easily and without requiring the addition or removal of additional components. For example, with a typical tracheostomy tube 10 and flange 30 as illustrated in FIG. 1, the addition of the retainer 60 described herein merely requires a user to (1) release a first strap 42 and pass it through the first strap hold 74 of the retainer 60 and reattach the strap 42, (2) release the second strap 42 and pass it through the second strap hold 76 and reattach the strap, and (3) place the retainer over the trach tube 10. Of course, the listed steps do not need to be performed in the described order. For example, the retainer 60 may be placed over the trach tube 10 first and then the straps 42 can be routed through the strap holds 74, 76 before being reattached. The straps 42 are preferably configured as described herein to allow efficient attachment and removal to allow quick and easy attachment and removal of the retainer 60, as desired.

Figure 4:
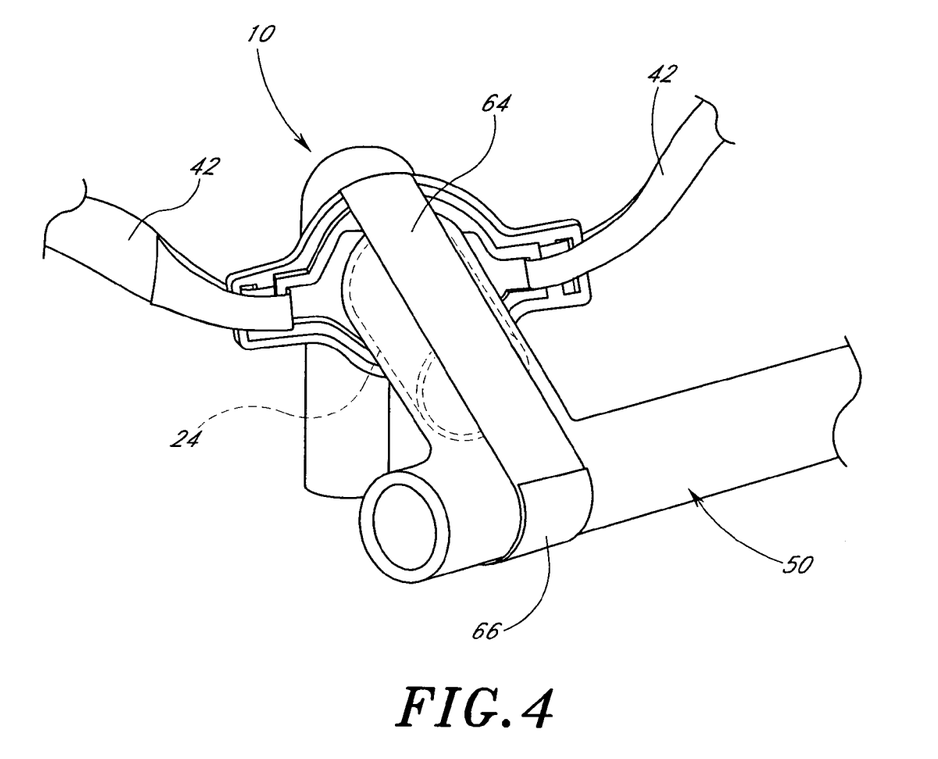
FIG. 4 shows the arrangement of FIG. 3 and further shows the securement device engaging an auxiliary device connected to the tracheostomy tube.

Referring to FIG. 4, an auxiliary device 50 is shown attached to the trach tube 10. Although the illustrated auxiliary device 50 is shown friction fit over the out tube 24, the auxiliary device 50 may be attached in any suitable manner. Once the auxiliary device 50 is connected to the trach tube 10 in a suitable manner, the upper strap 64 and lower strap 66 pass around the auxiliary device 50 and connect to one another. In the illustrated embodiment, the upper strap 64 and lower strap 66 are configured with hook and loop fastener and cooperate to securely grasp one another and hold the auxiliary device 50 in its attached configuration. Of course, in other embodiments, the upper strap 64 and lower strap 66 could be suitably configured with any type of fastening mechanism to allow the upper strap 64 and lower strap 66 to releasably and securely hold the auxiliary device 50 in its attached configuration. Alternatively, a single strap could be used to pass around the auxiliary device 50 and then connect to the retainer 60.

As an additional feature to securing the auxiliary device 50, once the upper strap 64 and lower strap 66 are appropriately tensioned about the auxiliary device 50, the straps 64, 66 oppose rotation of the auxiliary device about the trach tube 10. This further enhances the connection and inhibits undesirable movement.

As thus described, one embodiment of the retainer 60 is securely held against the trach tube flange 30 by the neck straps 42. In turn, the auxiliary device 50 is held to the trach tube 10 by the retainer 60 auxiliary straps 64, 66. Thus, in some embodiments, the auxiliary device 50 is connected to the flange 30 via the retainer 62 and can be attached or disconnected without disturbing the flange 30.

Figure 5:
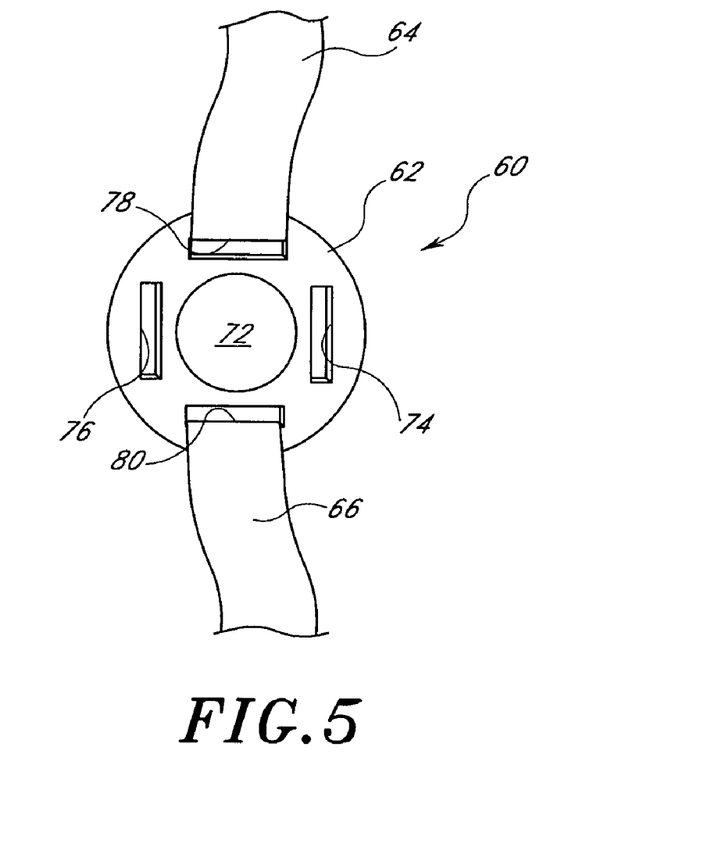
FIG. 5 is a plan view of an additional securement device embodiment.

FIG. 5 illustrates an additional embodiment of a retainer 60 having a ring 62, a void 72 defined within the central portion of the ring 62, lateral strap holds 74, 76 secondary strap holds 78, 80, and an upper strap 64 and a lower strap 66. In this embodiment, the ring is generally circular in shape and also defines a generally circular void 72. The void is preferably configured to allow passage of a trach tube 10 therethrough. The ring 62 defines a thickness between a front surface and a back surface. In one embodiment, the ring thickness is within the range of from about 0.0625 inches to about 0.125 inches or more.

The strap holds 74, 76 are defined by apertures formed through the ring 62. Likewise, the secondary strap holds 78, 80 are also formed by apertures through the ring 62. In some embodiments, the void 72 is specifically shaped to cooperate with a specific trach tube 10. For example, a trach tube can be configured with an annular ridge spaced away from the flange 30, in which case, the retainer 60 can be specifically configured with a void 72 that passes over the trach tube 10 but interferes with the ridge to space the retainer 60 away from the flange 30 a desired distance.

Figure 6:
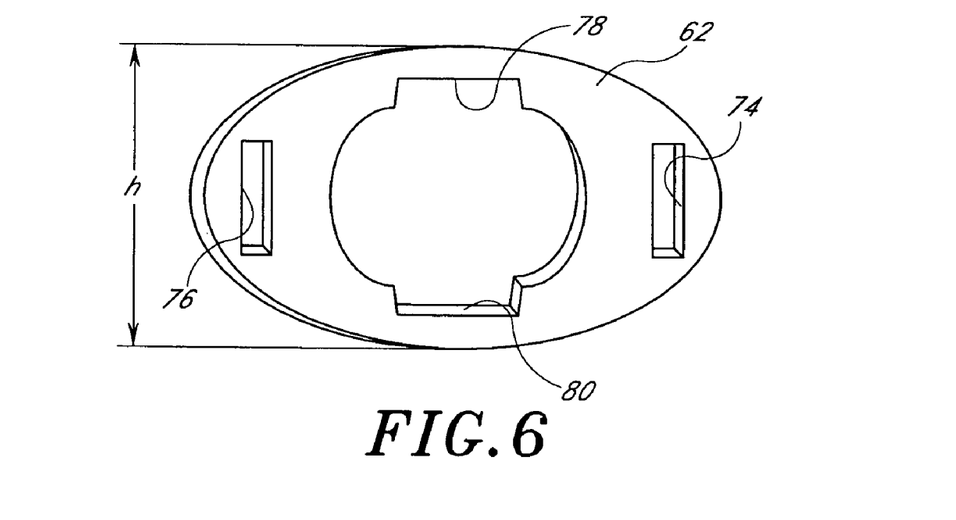
FIG. 6 is a plan view of an additional securement device embodiment.

FIG. 6 illustrates an additional embodiment of a ring 62 for use as a retainer 60 according to embodiments described herein. The ring is generally oval, or oblong, in shape. As such, the strap holds 74, 76 are spaced further apart than the secondary strap holds 78, 80. Such a configuration can be advantageous to influence the direction of forces acting on the ring because the spacing of the strap holds 74, 76 directly influences the magnitude of the force tending to urge the ring against the trach tube flange. In addition, spacing the strap holds 74, 76 allows for easier installation and removal of the retainer 60.

The tensioned neck strap 42 imparts a force onto the ring 62 that urges the ring 62 against the trach tube flange 30. Given a constant tension on the neck strap 42, the force is at a maximum when the neck strap 42 exerts a force in which the force vector is directly toward the trach tube flange 30, i.e. perpendicular to the plane of the flange 30. The force approaches zero as the force vector approaches a direction that is parallel to the plane defined by the front surface of the ring 62 and therefore only minimally urges the ring 62 against the trach tube flange 30. The direction of the force vector is controlled, in part, by the configuration of the ring 62.

As the ring 62 is reduced in size, such that the strap holds 74, 76 approach one another, the neck strap 42 is required to wrap more fully around the wearer's neck. As such, the neck strap 42 approaches the ring 62 from a direction that is nearly parallel to the plane of the ring 62, and thus, the force vector is likewise nearly parallel to the plane of the ring 62. Likewise, as the strap holds 74, 76 are spaced further apart, the neck strap 42 need not wrap completely around a wearer's neck and thus, approach the ring 62 from a direction that is perpendicular to the plane of the ring. For example, when the distance between the strap holds 74, 76 is equal to the diameter of a wearer's neck, the neck strap 42 will approach the ring at a direction that is directly perpendicular to the ring 62, and the force will reach a maximum. The above example assumes a flat, planar, ring, and is used for illustrative purposes only and not limiting. Of course, the ring 62 could be contoured to approximate the curvature of a wearer's neck, or otherwise curved so that it does not lie in a single plane.

As discussed above, spaced apart strap holds 74, 76, will apply a greater holding force urging the ring 62 against the flange 30 than if the strap holds 74, 76 are close together. However, in some preferred embodiments, the ring 62 is preferably not substantially larger than the trach tube flange 30.

It is desirable that the ring 62 not cause an excessive amount of discomfort to the patient. Thus, in some preferred embodiments, the height h of the ring is less than or equal to the height of the trach tube flange 30 so as to not further interfere with patient movement any more than the trach tube 10 alone.

With these considerations in mind, some preferred embodiments incorporate a ring 62 that distances the strap holds 74, 76 farther than the secondary strap holds 78, 80. In these embodiments, a major axis extends between the strap holds 74, 76 while a minor axis extends between the secondary strap holds 78, 80, with the major axis being greater than the minor axis. Some preferred ring shapes are oblong, oval, or rectangular in shape. Of course, the outer shape of the ring 62 may be circular or square and the void 72 can be configured to produce the desired spacing of the strap holds 74, 76. For example, with reference to FIG. 2, the ring 62 is substantially circular in shape and the configuration of the void 72 defines the spacing between the strap holds 74, 76 and the secondary strap holds 78, 80.

Figure 7:
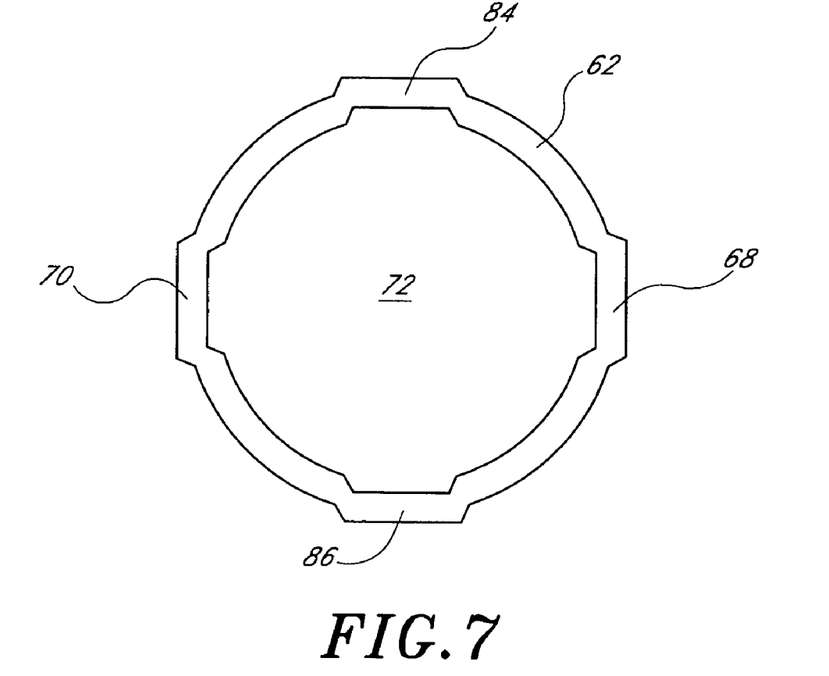
FIG. 7 is a plan view of another securement device embodiment.
Figure 8:
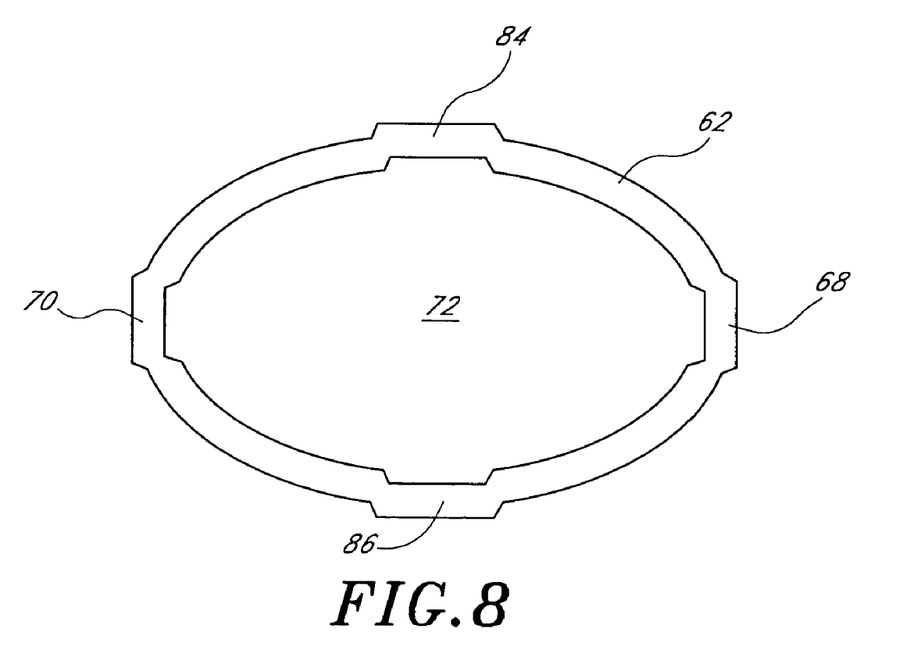
FIG. 8 is a plan view of yet another securement device embodiment.

FIGS. 7 and 8 illustrate yet additional embodiments of a ring 62 that can be used with the retainer described herein. In these additional embodiments, each ring 62 defines lateral extensions 68, 70 extending away from an otherwise circular or oval ring 62. Each embodiment further defines a top extension 84 and a lower extension 86 protruding from the ring 62. In each embodiment, the void 72 closely tracks the outer shape of the ring 62. The size of the void 72 will materially affect the strength of the ring 62, and hence, the ring 62 is preferably designed to withstand forces during normal use.

Although this invention has been disclosed in the context of certain preferred embodiments and examples, it will be understood by those skilled in the art that the present invention extends beyond the specifically disclosed embodiments to other additional embodiments and/or uses of the invention and obvious modifications and equivalents thereof. For example, while a few examplary embodiments have been shown and described herein, it will become readily apparent to those of skill in the art that several different ring shapes are capable of being used in conjunction with the claimed invention. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. An apparatus for securing an auxiliary device to a tracheostomy tube, the apparatus comprising:
   a ring having a pair of opposed extensions defining primary strap holds, and further having a pair of secondary strap holds;
   a void within the ring configured to allow passage of a tracheostomy tube through the ring, the ring extensions extending away from the void; and
   a pair of auxiliary device straps affixed to each of the secondary strap holds, the auxiliary straps configured so that, when the tracheostomy tube extends through the ring void, the auxiliary straps extend around an auxiliary device that is fit onto the tracheostomy tube so as to maintain a maximum spatial relationship between the auxiliary device and the ring;
   wherein the primary strap holds are spaced farther apart than the secondary strap holds.

2. The apparatus of claim 1, wherein the auxiliary device straps are configured with fastening elements to releasably secure the auxiliary device straps together.

3. The apparatus of claim 2, wherein the fastening elements comprise hook and loop fasteners.

4. The apparatus of claim 1, wherein the ring has a major axis extending between the primary strap holds and a minor axis extending between the secondary strap holds, and the major axis is greater than the minor axis.

5. The apparatus of claim 1 in further combination with a tracheostomy collar having a neck strap and wherein the neck strap engages the ring so that the ring is secured to the tracheostomy collar by the neck strap.

6. The apparatus of claim 5, wherein the neck strap comprises an elongate member that simultaneously connects to the tracheostomy collar and extends through the ring primary strap holds.

7. An apparatus for securing an auxiliary device to a tracheostomy tube, the apparatus comprising:
   a ring having a pair of opposed extensions defining primary strap holds, and further having a pair of secondary strap holds;
   a void within the ring configured to allow passage of a tracheostomy tube through the ring, the ring extensions extending away from the void;
   a pair of auxiliary device straps affixed to each of the secondary strap holds, the auxiliary straps configured so that, when the tracheostomy tube extends through the ring void, the auxiliary straps extend around an auxiliary device that is fit onto the tracheostomy tube so as to maintain a maximum spatial relationship between the auxiliary device and the ring; and
   a tracheostomy collar having a neck strap;
   wherein the neck strap engages the ring so that the ring is secured to the tracheostomy collar by the neck strap.

8. The apparatus of claim 7, wherein the neck strap comprises an elongate member that simultaneously connects to the tracheostomy collar and extends through the ring primary strap holds.

9. A method of securing an auxiliary device to a flanged tracheostomy tube, comprising the steps of:
   providing a flanged tracheostomy tube;
   providing an auxiliary device;
   providing a tracheostomy collar having an elongate neck strap, the flanged tracheostomy tube comprising opposed neck strap holds configured to accommodate the neck strap;
   providing a retainer configured to fit over the tracheostomy tube, the retainer having a retainer strap configured for releasable engagement with the auxiliary device, and further having two or more primary strap holds configured to receive the neck strap;

fitting the retainer over the tracheostomy tube;

securing the neck strap to the flanged tracheostomy tube neck strap holds and simultaneously to the retainer primary strap holds, thereby securing the retainer to the tracheostomy tube;

engaging the auxiliary device with the tracheostomy tube; and securing the retainer to the auxiliary device with the retainer strap.

10. The method of claim 9, wherein the tracheostomy tube strap holds comprise slots, and the elongate neck strap passes through the slots and also passes through the primary strap holds on the retainer.

11. The method of claim 10, wherein the retainer has a major axis and a minor axis, the major axis being greater than the minor axis, and the primary strap holds are arranged along the major axis.

12. The method of claim 9, wherein the securing the retainer to the auxiliary device step comprises fastening a pair of retainer straps having a hook and loop fastening closure around the auxiliary device.

13. An apparatus for securing an auxiliary device to a tracheostomy tube, the apparatus comprising:

a ring having an aperture, a pair of opposed primary strap holds, and a pair of secondary strap holds; and a pair of auxiliary device straps affixed to each of the secondary strap holds, the auxiliary straps configured so that, when the tracheostomy tube extends through the ring aperture, the auxiliary straps can extend around an auxiliary device that is fit onto the tracheostomy tube so as to maintain a maximum spatial relationship between the auxiliary device and the ring;

wherein a tube accepting portion of the aperture is shaped to generally correspond to a tracheostomy tube so as to allow passage of a tracheostomy tube through the ring, the tube accepting portion of the aperture and the primary strap holds being defined by a single aperture formed through the ring; and wherein the ring is configured so that a space is defined between each primary strap hold and the tube accepting portion of the aperture so that a strap can be fit onto each of the primary strap holds when the tube accepting portion of the aperture is occupied by a tracheostomy tube.

14. The apparatus of claim 13, wherein the single aperture comprises a major axis and a minor axis, the major axis being greater than the minor axis, and the primary holds are disposed along the major axis.

15. The apparatus of claim 14, wherein the primary holds comprise a generally flat surface configured to accommodate a strap.

16. The apparatus of claim 13, wherein the ring aperture has an inside surface, and the primary strap holds are defined by indentations formed in the inside surface.

17. The apparatus of claim 16 in further combination with a tracheostomy collar having a neck strap and wherein the neck strap engages the ring so that the ring is secured to the tracheostomy collar by the neck strap.

18. The apparatus of claim 17, wherein the neck strap comprises an elongate member that simultaneously connects to the tracheostomy collar and extends through the ring primary strap holds.

19. The apparatus of claim 16, wherein the ring is unitarily formed as a single piece.

20. A tracheostomy tube apparatus, comprising:

a tracheostomy tube having a flange, the flange having a major axis and a minor axis, the major axis being greater than the minor axis, and a pair of collar apertures are disposed along the major axis;

a collar comprising a strap adapted to fit about a wearer's neck and adapted to fit through the collar apertures; and an auxiliary device securement apparatus, comprising:

a ring having an aperture, a pair of opposed primary strap holds, and a pair of secondary strap holds; and a pair of auxiliary device straps affixed to each of the secondary strap holds, the auxiliary straps configured so that, when the tracheostomy tube extends through the ring aperture, the auxiliary straps can extend around an auxiliary device that is fit onto the tracheostomy tube so as to maintain a maximum spatial relationship between the auxiliary device and the ring;

wherein a tube accepting portion of the aperture is shaped to generally correspond to a tracheostomy tube so as to allow passage of a tracheostomy tube through the ring; and wherein the ring is configured so that a space is defined between each primary strap hold and the tube accepting portion of the aperture so that a strap can be fit onto each of the primary strap holds when the tube accepting portion of the aperture is occupied by a tracheostomy tube;

wherein the collar strap is fit through the collar apertures and the ring primary strap holds so as to secure the ring relative to the flange.

21. The apparatus of claim 20, wherein the ring has a major axis and a minor axis, the ring minor axis being no greater than the flange minor axis.

22. The apparatus of claim 21, wherein the ring major axis is greater than the ring minor axis.

23. The apparatus of claim 22, wherein the primary strap holds are each defined by a primary strap hold aperture formed through the ring.

24. The apparatus of claim 22, wherein the tube accepting portion of the aperture and the primary strap holds are defined by a single aperture formed through the ring.

25. The apparatus of claim 24, wherein the ring aperture has an inside surface, and the major strap holds are defined by indentations formed in the inside surface.

26. An apparatus for securing an auxiliary device to a tracheostomy tube, the apparatus comprising:

a ring having an aperture, a pair of opposed primary strap holds, and a pair of secondary strap holds, the primary strap holds each being defined by a primary strap hold aperture formed through the ring; and a pair of auxiliary device straps affixed to each of the secondary strap holds, the auxiliary straps configured so that, when the tracheostomy tube extends through the ring aperture, the auxiliary straps can extend around an auxiliary device that is fit onto the tracheostomy tube so as to maintain a maximum spatial relationship between the auxiliary device and the ring;

wherein a tube accepting portion of the aperture is shaped to generally correspond to a tracheostomy tube so as to allow passage of a tracheostomy tube through the ring; and wherein the ring is configured so that a space is defined between each primary strap hold and the tube accepting portion of the aperture so that a strap can be fit onto each of the primary strap holds when the tube accepting portion of the aperture is occupied by a tracheostomy tube.

27. The apparatus of claim 26, wherein the aperture comprises a major axis and a minor axis, the major axis being greater than the minor axis, and the primary holds are disposed along the major axis.

* * * * *